United States Patent [19]

John

[11] 4,216,781

[45] Aug. 12, 1980

[54] METHODS OF ELECTROPHYSIOLOGICAL TESTING

[76] Inventor: E. Roy John, 930 Greacen La., Mamaroneck, N.Y. 10546

[21] Appl. No.: 918,731

[22] Filed: Jun. 26, 1978

[51] Int. Cl.³ .............................................. A61B 5/04
[52] U.S. Cl. .................................. 128/731; 35/35 R
[58] Field of Search ...................... 128/731, 732, 630; 351/39; 35/35 R, 35 C

[56] References Cited

U.S. PATENT DOCUMENTS

| | | | |
|---|---|---|---|
| 3,570,145 | 3/1971 | Hickey | 35/35 R |
| 3,892,227 | 7/1975 | Coursin et al. | 128/731 |
| 3,893,450 | 7/1975 | Ertl | 128/731 |
| 3,901,215 | 8/1975 | John | 128/731 |

OTHER PUBLICATIONS

"A Simple Visual Pattern Stimulator"–by: B. T. Evans, et al., *Electroencephalography & Clinical Neurophysiology*, vol. 37, No. 4, pp. 403–406; Oct. 1974.

*Primary Examiner*—Willis Little
*Attorney, Agent, or Firm*—Eliot S. Gerber

[57] ABSTRACT

In electrophysiology, methods of testing a subject's neural mechanisms of learning and memory in order to quantitatively diagnose the subject's brain dysfunction require specified conditions or stimuli to evoke his electrical brain activity, which are his response or non-response to the stimuli. These evoked responses are quantitatively interpreted by challenges which specify analytic protocol. A test using letter reversal conditions identifies a subject's problems relating to pattern reversal and perception. A test involving figure-ground condition in which a primary stimulus is obscured with secondary stimuli indicates a subject's ipsimodal and cross-modal inhibition. A test using a standard-interruptive condition, in which a series of standard and interruptive stimuli are alternated, indicates a subject's conditionability, sensitization and recovery cycle.

11 Claims, 4 Drawing Figures

METHODS OF ELECTROPHYSIOLOGICAL TESTING

BACKGROUND OF THE INVENTION

The present invention related to electrophysiology (electroencephalography, class 128, subclass 2.1 B), and more particularly to the testing of neural mechanisms of learning and memory to quantitatively diagnose brain dysfunction.

It is known that specified conditions or stimuli may be used to evoke brain electrical activity, which may be detected, indicating the subject's response or non-response to the stimuli. The evoked responses may be quantitatively interpreted by "challenges" which specify analytic protocol.

An article by Shigeru Yosida et al, July 1975, *Electroencephalography and Clinical Neurophysiology,* states that the averaged evoked response produced by a stationary grating of alternating high dark-bright contrast was less in amplitude when it was presented obliquely than when it was oriented horizontally or vertically. Additionally, the amplitude varied on oblique orientation. However, this test indicated only that vertical and horizontal orientation elicit larger responses in that they are identifiable or the brain is more certain of their orientation. The brain recognizes vertical and horizontal orientations but assimilates oblique orientations. Even assuming an even number of dark and bright areas, 180° rotation would produce only minimal pattern reversal and is clearly of insignificant meaning as a control for that purpose.

In the U.S. Pat. No. 3,780,274 entitled "Sensation-Cognition Computer" there is disclosed quantitative electrophysiological tests having the three general components. These three general components are: (i) a sensory stimulus is presented to the subject, such as a series of light flashes in a defined order; (ii) a recording is made of the subject's brain waves in response to the stimulus; and (iii) a computer-based digital analysis of the responsive brain waves compares the subject's responses to values obtained from testing of prior subjects. The tests described in that patent are of ordered sequence vs. random sequence; predictable pattern and its alternation; habituation and dishabituation to the same meaningless stimulus; and conditioning using different senses and presentation of different geometric designs.

The U.S. Pat. No 3,906,644 entitled "Method of Presenting Reading Material To Dysmetric Dyslexic-Identified Children" discusses the problem of letter reversals and confusion of words and letters which differ in spacial placement.

SUMMARY OF THE INVENTION

The present invention is directed to three methods which may be used to quantitatively aid in the diagnosis of brain dysfunction.

Electrophysiological methods of testing neural mechanisms of learning and memory to quantitatively diagnose brain dysfunction require specified stimuli. The subjects to be tested are generally equipped with an array of electrodes which are attached to the skull surface and which sense the evoked electrical brain responses.

The first method is to present a visual display of a series of known, individually identifiable symbols which have specific meanings in various orientations, wherein the inability to distinguish between the symbols is characteristic of certain brain dysfunction. A specific embodiment of the invention uses a letter reversal condition, in which the letters "d", "b", "p", "q" are individually presented to the subject. The subject's brain wave responses are indicative of pattern reversal, recognition and perception problems.

The second method is to present the subject with primary and secondary stimuli at the same time and then present the secondary stimuli alone, wherein the inability to suppress the secondary stimuli with respect to the primary stimuli is characteristic of certain brain dysfunction. The second method is a figure-ground condition in which a primary stimulus, such as video display, is obscured by secondary visual, auditory and somatosensory stimuli and is indicative of ipsimodal and cross-modal inhibition.

The third method is to present the subject with alternating series of standard and interruptive stimuli. The interruptive series includes conditioned and unconditioned stimuli and the responses to the conditioned and unconditioned stimuli indicate conditionability, sensitization and recovery cycle. This third method is a "standard-interruptive" condition in which standard and interruptive series of stimuli are alternated.

OBJECTIVES AND FEATURES OF THE INVENTION

It is an objective of the present invention to provide electrophysiological methods for testing neural mechanisms of learning and memory which may be used as quantitative indicators of brain dysfunction.

It is another objective of the present invention to provide a method in which responses evoked by individually identifiable and meaningful patterns (symbols) may indicate a subject's inability to distinguish between the patterns and may be characteristic of such dysfunctions as pattern reversal and perceptive learning disabilities.

It is another objective of the present invention to test a subject's ipsimodal and cross-modal inhibition ability by interrogation using simultaneously presented primary and secondary stimuli and comparing the subject's responses to those generated by the isolated presentation of secondary stimuli.

It is another objective of the present invention to provide a method in which conditionability, sensitization and recovery cycles may be interrogated by presenting alternating series of standard and interruptive stimuli and evoking conditioned and non-conditioned responses.

The methods of the present invention utilize easily reproducible auditory, visual and somatosensory stimuli. The stimuli protocols for interrogating neural learning and memory mechanisms are standardized for comparison with the responses of prior subjects, those responses forming a quantitized set of norms.

The evoked responses may be efficiently sensed by an array of electrodes attached to the subject's skull surface. The evoked responses may be recorded in graphical or digital form. The evoked response may be used to establish a control group of responses which later may be used as the basis of comparative analysis.

DESCRIPTION OF THE DRAWINGS

Other features and objectives of the present invention will be apparent from the following detailed description of the preferred embodiment taken in conjunction with the accompanying drawings.

In the drawings.

DETAILED DESCRIPTION OF THE INVENTION

Figure 1:
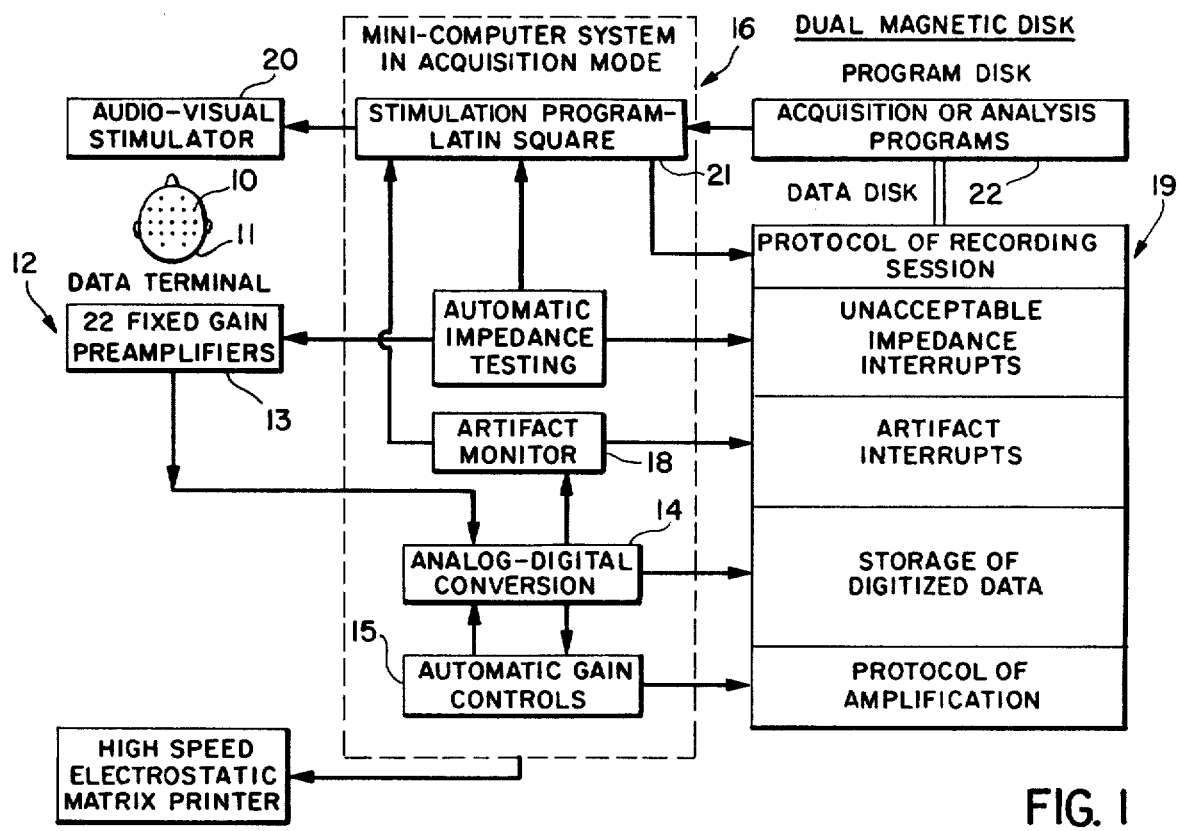
FIG. 1 is a block diagram of the digital computer based system utilized in connection with the methods of the present invention.

The methods of the present invention, which are described below, may be used in the system shown in the accompanying FIG. 1, in which a plurality of electrodes 10 are placed on the head 11 of the subject under test. Preferably the electrodes are placed anatomically in accordance with the International Association 10-20 System. That system provides 19 electrodes which are removably attached to the head, preferably by paste, and which provide an indication of the subject's brain waves at the 19 locations on the scalp to which the electrodes are attached.

Each of the electrodes is attached to a data terminal which includes a set of fixed gain preamplifiers 13, with one preamplifier connected to each electrode. There are nineteen fixed gain preamplifiers corresponding to the nineteen electrodes attached to the head to detect brain waves and three preamplifiers connected to electrodes attached to other portions of the subject to detect muscle artifact, electrocardiogram (EKG) or respiration.

The impedances of the electrodes are automatically tested by automatic impedance testing means 23 to insure that there is a good contact between the scalp of the subject and the electrode. Generally it is preferable that the impedance be below 5000 ohms at each electrode. If the impedance exceeds a predetermined level, for example, 50,000 ohms, the signals from that electrode may be blanked out, i.e., not recorded.

The preamplifiers 13 are connected to the analog-to-digital converter 14. There are a number of commercially available variable gain A-D converters suitable for this purpose. Preferably a single A-D converter is used which, in effect, multiplexes each of the channels and digitizes their output in sequence. The analog digital converter 14 is controlled by an automatic gain control 15 so that each input signal has an individual variable gain up to a factor of 256. The computer system 16 provides a program control gain protocol to set the variable gain for each of the EEG channels. Further details concerning this protocol, as well as other portions of the systems described herein, may be found in the inventor's book, *Functional Neuroscience*, Volume II, "Neurometrics: Clinical Applications of Qualitative Electrophysiology," published 1977 by Lawrence Erlbaum Associates, and particularly its Chapter 4, pages 75 through 85. That volume, and particularly the above-mentioned pages, are incorporated by reference herein.

The computer system 16 may be based on a PDP 11-10 computer or 11-03 microprocessor and includes an artifact monitor 18 which detects and rejects muscle artifact, movements or other amplitude excursions which would tend to distort the brain wave information. The computer system 16 is connected to a multi-channel recording media which is preferably a magnetic disk. The disk 19 records, as shown in the figure, the protocol of the recording session, the unacceptable impedance interrupts, the artifact interrupts, the storage of digitized data, and the protocol of the amplification.

The subject under test views an audio-visual stimulator 20. For example, the audio-visual stimulator may be a television screen and, in addition, an audio amplifier and a light flasher. The stimulator 10 provides a programmed set of stimuli to the subject under test, such as a series of grid squares shown on a screen, a series of lights or a series of clicks. The stimulator receives its instructions from the stimulation program 21. Programming of the computer system 16 in its acquisition mode, i.e., when it is acquiring brain wave information from the subject under test, is preferably obtained from a program magnetic disk 22.

METHOD NUMBER ONE

In accordance with the present invention a first method of the neurometric test battery interrogates the subjects condition-ability, sensitization and recovery cycle. Generally, alternating series of standard and interruptive stimuli are presented to the subject. The interruptive condition comprises a paired combination of conditioned and unconditioned stimuli in which the conditioned stimulus elicits the unconditioned stimulus response. The ability to generate the unconditioned stimulus response in the absence of unconditioned stimulus indicates the subject's conditionability. The ability to respond independently to a stimulus similar to the unconditioned stimulus at a later time indicates the subject's sensitization. Both conditionability and sensitization are based on the subject's responses to the standard series of stimuli and as altered by conditioned and unconditioned stimuli. Recovery cycle is based on the subject's ability to adapt and respond to the unconditional response of the interruptive series.

Figure 2:
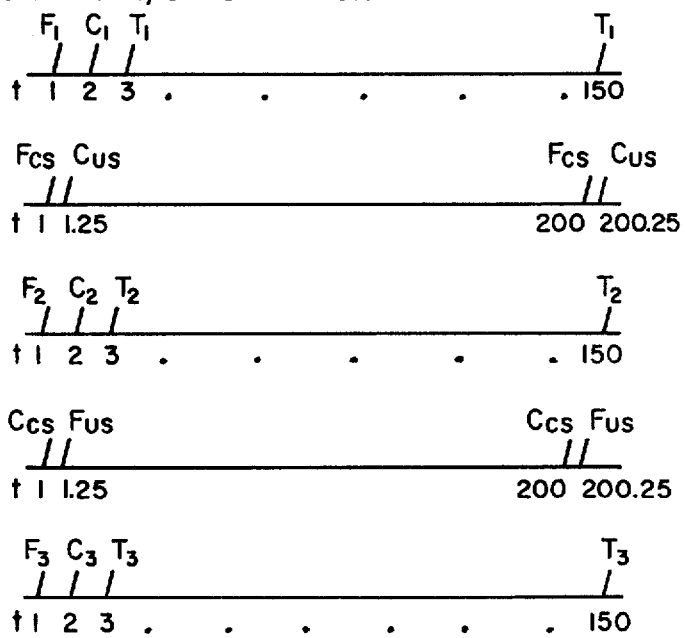
FIG. 2 is a graphical representation of time stimuli relation of the third method.

In one embodiment of the present invention, shown in FIG. 2, the standard condition comprises a three stimuli series of Flash (F), Click (C), Tap (T) spaced at 1 sec. intervals. The series is repeated 50 times presenting a total of 150 stimuli to the subject. This condition is used three times in alternation with the interruptive condition. The first standard condition responses are designated as $F_1 C_1 T_1$; the second standard condition responses are designated $F_2 C_2 T_2$; and the third standard condition responses are designated $F_3 C_3 T_3$. The first interruptive response follows the first standard condition and comprises a Flash (conditioned stimulus) (Fcs), followed 250 msec later by a Click (unconditioned stimulus) (Cus). The second interruptive series between the second and third standard condition comprises a Click (conditioned stimuli) (Ccs), followed by a Flash (unconditioned stimulus) (Fus) 250 msec later. Each interruptive condition is repeated 200 times.

The subject's conditionability is measured by comparing the response to $F_1$ with the response to $F_2$, indicating the extent to which the subject's response has been conditioned, that is, the extent to which the subject will expect the flash to be followed by a click 250 msec later. The extent to which the response to $F_2$ is similar to the response to Fcs (eliciting an unconditioned and unstimulated response similar to a response to Cus) is a measure of the subject's ability to adapt to visual conditioning. A similar analysis may be performed with respect to $C_3$ and $C_2$ indicating the conditioned auditory response.

Sensitization, on the other hand, measures the subject's ability to independently respond to a stimulus similar to the unconditioned stimulus. For instance, comparison of the responses to clicks ($C_2$ and $C_1$) before and after F-C pairing (the first interruptive condition) shows sensitization effects on the unconditioned stimulus Cus. More particularly, such comparison will indicate the subject's ability to distinguish the clock $C_2$ independent of the unconditioned stimulus $C_{us}$. Comparison of the responses to Tap before and after F-C pairing show nonspecific changes unrelated to pairing per se, such as changes in arousal or habituation. Analogous measures are available after C-F pairing (the second interruptive condition). In general, one expects to find US-like (unconditioned stimulus) responses being elicited by the CS on cortical regions specifically related to the modality of the US. These changes are quantified in the following manner: $(F_2-F_1)/F_1 = \%$ conditioned visual response; $(C_2-C_1)/C_1 = \%$ sensitization; $(T_2-T_1)/T_1 = \%$ nonspecific change; $(C_3-C_2)/C_2 = \%$ conditioned auditory response; $(F_3-F_2)/F_2 = \%$ sensitization; $(T_3-T_2)/T_2 = \%$ nonspecific change.

The recovery cycle is based on the subject's ability to adapt and independently respond to the unconditioned stimulus. Specifically, the response to $C_{us}$ during F-C pairing (first interruptive condition) is compared with the response to $C_1$ alone before F-C pairing. Differences are quantified and reflect the diminution in response to $C_{us}$ because of incomplete recovery from $F_{CS}$ and lag in the cross-sensory shift. Similarly, the response to $F_{us}$ during second interruptive condition (C-F pairing) is compared to the response to $F_2$ alone. The differences are quantified and reflect the dimunition in response to $F_{us}$ because of incomplete recovery to $C_{us}$ and the lag in cross-sensory shift. These measures can be conceptualized as an index of a perceptual moment of inertia, reflecting the ease with which attention can shift from modality to modality.

METHOD NUMBER TWO

A figure-ground condition and challenge of the neurometric test battery is established by presenting the subject with a primary visual, auditory or somatosensory stimuli. Generally people have been known, when listening to a concert, to distinguish, for instance, the sound of the bassoon or the French horn from all other instruments. Other people have been known to watch and absorb a T.V. program even though the screen is covered with "snow". The ability to concentrate the senses on a particular sensory stimulus is indicative of the ipsimodal and cross-modal inhibition.

The instant invention presents an electrophysiological method of testing the subject's ipsimodal and cross-modal inhibition capability. Although any sense may be used for primary stimulation, the visual and auditory senses are preferred as these are particularly easy to work with.

Figure 3:
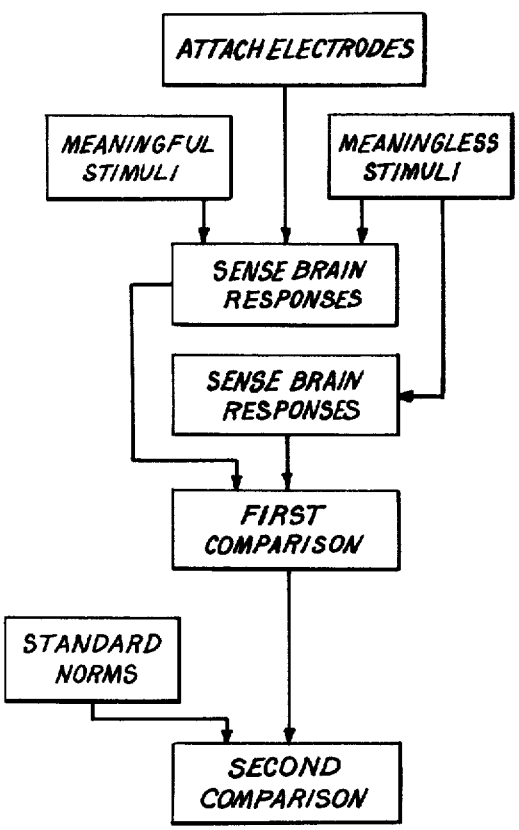
FIGS. 3 and 4 are block flow diagrams of the embodiments of the methods of the present invention.

In accordance with the present invention, as illustrated in FIG. 3, a primary stimulus, such as a video display, is presented to the subject while he is also exposed to a specified pattern of secondary meaningless and irrelevant auditory, visual and somatosensory stimuli. The subject's ability to concentrate on primary stimulus, and consequently suppress his perception of the secondary stimuli, indicates his inhibition capability. The electrical brain responses generated during the combined figure and ground condition are sensed and recorded. The subject is then exposed to the same series of secondary meaningless and irrelevant visual, auditory and somatosensory stimuli. The electrical brain responses generated by this ground condition are sensed and recorded. A comparison of evoked responses to the figure-ground condition and to the ground condition indicates the subject's ability to suppress irrelevant information. If the primary stimulus is visual and the secondary suppressed stimulus is visual, the test would measure the subject's ipsimodal visual inhibition capability. Similarly, if the primary stimulus is auditory and secondary stimulus is auditory, the test would measure the ipsimodal auditory inhibition capability. Alternatively, if the stimulus is visual and the suppressed secondary stimulus is auditory, the test would measure the cross-modal visual auditory inhibition capability. In general, this technique can be used with all five senses, one constraint being the physical ability to reproduce the particular stimuli. Generally, if x is the number of primary senses stimulated and y is the number of secondary senses stimulated, then (x·y) will represent the total number of ipsimodal and cross-modal inhibition factors generated.

METHOD NUMBER THREE

In the letter reversal condition and challenge of the neurometric test battery, a specified serial display of individually meaningful paired shapes are presented to the subject. For example, they are shown on a television screen or a slide projector screen. These shapes are characteristically selected on the criteria that one shape is the reverse of the other, such as the pair of letters "b" and "d" and the pair of letters "p" and "q". The subject's brain, upon perception and recognition of these letters, will generate detectable electrical responses which permit a computer-based estimate of the subject's ability to discriminate between shapes.

Figure 4:
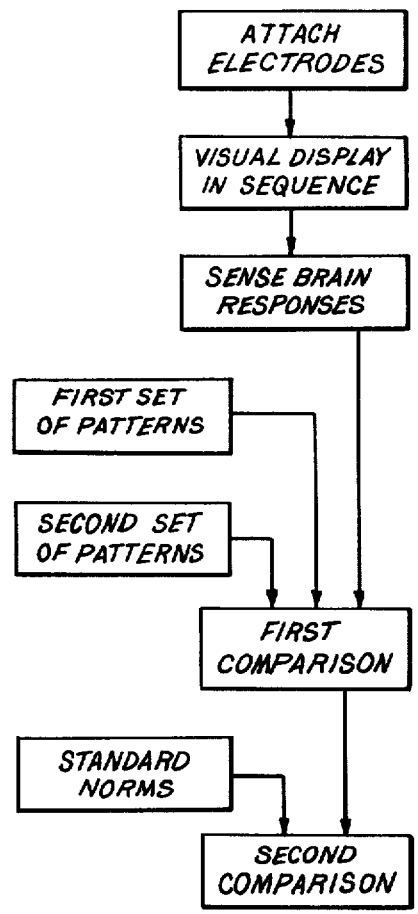

The third method of the instant invention, as illustrated in FIG. 4, is directed to perception and recognition of reversed patterns. More particularly, "b" is interpreted as "bee", the second letter of the alphabet, and not the reverse "d", i.e., "dee", the fourth letter of the alphabet. Thus, the difference between letter "b" and "d" is analogous, in physical outline, to the difference between a geometric circle and a square or a vertical and a horizontal line. However, the value of the present method is that certain subjects are unable to distinguish between "b" and "d", although they are able to distinguish geometric circles and squares.

The method of the present invention causes the subject to generate individually identifiable electrical responses for each letter presented. The response for each letter will be distinguishable from the responses for other letters if the subject's perception and recognition are normal. For instance, a dyslexic subject might generate the same response for both the letters "b" and "d". A skilled technician, using the method of the present invention, can easily distinguish between normal perception and recognition responses, and thereby easily identify those subjects with pattern perception and reversal problems.

Accordingly, the instant invention presents a method of testing for pattern perception and reversal problems in which a visual display of a series of individually identifiable letters is presented to a subject. The letter configuration for all letters is the same and the specific orientation of the configuration elicits the unique recognition response. The subject's ability to reproducibly generate this unique response for the particular letter is indicative of the subject's pattern reversal, recognition and perceptual powers. Although the preferred embodiment of the present invention includes the four letters "b", "d", "p", "g" which are distinguished by their orientation, other letters or number combinations such as 6, 9, W, M and the mathematical symbols >, <, may also be used.

2. A method as in claim 1 wherein the primary stimulus is a visual display and the secondary stimuli are auditory, visual and somatosensory.

3. A method as in claim 1 wherein said primary stimulus is an audio recording and said secondary stimuli are

Table

Present content of the neurometric test battery with a brief indication of the intended purpose of each item.

| Neurometric test item | Intended purpose |
| --- | --- |
| EEG conditions and challenges | |
| 1. Eyes open, spontaneous EEG | Baseline measures |
| 2. Eyes closed, resting EEG | Yields age-dependent quotient |
| 3. Eyes open minus eyes closed | Effect of removal of visual input |
| 4. Photic driving at 2.5, 5, 10, and 18 hertz | Yields reactivity in delta, theta, alpha, and beta ranges when compared with baseline measures |
| AER conditions and challenges | |
| Sensory acuity | |
| 5. 65 lines per inch, 50 percent transmission | Percieved as a blank flash |
| 6. 27 lines per inch, 50 percent transmission | Seen as checkerboard if visual acuity is approximately 20/20 |
| 7. 7 lines per inch, 50 percent transmission | Seen as checkerboard unless visual acuity is worse than 20/200 |
| 8. 45 db click | Elicits auditory AER unless hearing loss is sufficiently severe to interfere with language acquisition |
| Pattern perception | |
| 9. Large square | Each contributes to an estimate of perception of differences in geometric forms but preservation of shape invariance independent of size |
| 10. Small square | |
| 11. Large diamond | |
| 12. Small diamond | |
| 13. "b" | Each contributes to estimates of central discrimination between shapes of letters most commonly reversed |
| 14. "d" | |
| 15. "p" | |
| 16. "q" | |
| Prediction of temporal order | |
| 17. Random versus regular flash | Change in AER waveshape reflects diminished response to predictable stimuli, indicates recognition of repeated temporal sequence |
| 18. Random versus regular click | |
| 19. Random versus regular tap | |
| 20. Phasic habituation | Reveals rate and amount of suppression of information input about a meaningless monotonous event, reflects attention and short-term memory |
| 21. Dishabituation | Indicates whether suppressed input is nonetheless continuously monitored to permit detection of possible change |
| 22. Rehabituation | By comparison with initial phasic habituation, reveals whether suppression of meaningless input is facilitated by memory of previous experience |
| Sensory-sensory interactions | |
| 23-25. Passive interactions between visual, auditory, and somatosensory systems | Reveals increase or decrease in response of brain as a result of simultaneous presentation of simple stimuli in different sensory modalities |
| 26. Flash followed by click 250 msec later | Measure of recovery cycle after visual input |
| 27. Click followed by flash 250 msec later | Measure of recovery cycle after auditory input |

What is claimed is:

1. A method of testing subjects to characterize the subject's ability to inhibit sensory stimulation which comprises:
   (a) attaching electrodes to the subject's head and presenting the subject with primary meaningful sensory stimulus,
   (b) simultaneously superimposing secondary meaningless sensory stimuli on said primary sensory stimulus,
   (c) sensing the electrical brain responses of the subject,
   (d) presenting the subject with said secondary stimuli without said primary stimulus,
   (e) sensing the subject's electrical brain responses,
   (f) making a first comparison using a digital computer-based system of the responses evoked by said primary and secondary stimuli with the responses evoked by said secondary stimuli alone, and
   (g) making a second comparison using a digital computer-based system of said first comparison with a set of standard norms as an indication of the subject's ability to inhibit secondary stimuli.

auditory, visual and somatosensory.

4. A method of testing subjects to identify pattern perception and reversal problems which comprises:
   (a) attaching electrodes to the subject's head and presenting to the subject a visual display in sequence of a series of known, individually identifiable patterns comprising the pairs of letters and numbers selected from the set comprising "p", "q" and "d", "b" and "6", "9" and "M", "W" which have specific meanings in a specific orientation;
   (b) sensing the subject's electrical brain response;
   (c) making a first comparison using a digital computer-based system of the subject's responses to a first set of known identifiable patterns at specific orientations, for example, "d", "b", with a second and associated set of such patterns, for example, "d", "d", and
   (d) making a second comparison using a digital computer-based system of said first comparison with a set of standard norms to characterize the subject's pattern reversal, recognition and perceptual powers.

5. A method of testing subjects to identify conditionability and sensitization which comprises:
   (a) subjecting the subject to specified alternating series of standard and interruptive stimuli, said standard stimuli comprising a first series of regularly repeated selected stimuli and said interruptive stimuli, a second series of regularly repeated stimuli which differs from said first series and has two different stimuli in each member of the series;
   (b) sensing the subject's electrical brain responses;
   (c) making a first comparison using a digital computer-based system to determine the subject's responses to said interruptive stimuli on the response to said standard stimuli; and
   (d) making a second comparison using a digital computer-based system to determine the deviation of the first comparison from a set of standard norms.

6. A method as in claim 5 wherein said standard series of stimuli comprises a flash, click and tap each separated by 1 sec. and repeated 50 times to produce 150 individual stimuli.

7. A method as in claim 5 wherein the first interruptive stimuli series comprises 200 paired flash-click combinations where said flash is followed by a click 250 msec. later.

8. A method as in claim 5 wherein the second interruptive stimuli series comprises 200 paired click-flash combinations where said click is followed by a flash 250 msec later.

9. A method of interrogating subjects to characterize the recovery cycle which comprises:
   exposing the subject to a specified alternating series of standard and interruptive stimuli,
   sensing the electrical brain responses, and
   comparing the response to the unconditioned stimulus to the response to the standard stimulus,
   wherein said standard series of stimuli comprises a flash, click and tap each separated by 1 sec and repeated 50 times to produce 150 individual stimuli.

10. A method as in claim 9 wherein a first interruptive stimuli series comprises 200 paired flash-click combinations where said flash is followed by a click 250 msec later.

11. A method as in claim 9 wherein a second interruptive stimuli series comprises 200 paired click-flash combinations where said click is followed by a flash 250 msec later.

* * * * *